United States Patent [19]

Bolich, Jr.

[11] 4,387,090

[45] Jun. 7, 1983

[54] HAIR CONDITIONING COMPOSITIONS

[75] Inventor: Raymond E. Bolich, Jr., Maineville, Ohio

[73] Assignee: The Procter & Gamble Company, Cincinnati, Ohio

[21] Appl. No.: 234,271

[22] Filed: Feb. 13, 1981

Related U.S. Application Data

[63] Continuation-in-part of Ser. No. 218,372, Dec. 22, 1980, abandoned, which is a continuation-in-part of Ser. No. 128,437, Mar. 10, 1980, abandoned.

[51] Int. Cl.$^3$ .................. A61K 7/06; A61K 31/74; A61K 31/745
[52] U.S. Cl. .................................. 424/70; 424/78; 424/81; 424/83
[58] Field of Search .................. 424/70, 78, 83, 81

[56] References Cited

U.S. PATENT DOCUMENTS

| | | |
|---|---|---|
| 2,826,551 | 3/1958 | Geen . |
| 3,439,088 | 4/1969 | Edman . |
| 3,577,528 | 5/1971 | McDonough et al. . |
| 3,818,105 | 6/1974 | Coopersmith et al. . |
| 3,932,610 | 1/1976 | Rudy et al. . |
| 3,950,510 | 4/1976 | Adams . |
| 3,964,500 | 6/1976 | Drakoff ................................ 424/81 |
| 4,053,581 | 10/1977 | Pader et al. ............................ 424/68 |

FOREIGN PATENT DOCUMENTS

| | | |
|---|---|---|
| 666421 | 4/1967 | South Africa . |
| 676049 | 3/1968 | South Africa . |
| 849433 | 9/1960 | United Kingdom . |
| 2025228 | 1/1980 | United Kingdom . |

OTHER PUBLICATIONS

"Silicones Provide Real Benefits for Aerosol Cosmetics," Todd, C. W. and Hayes, S., American Perfumer and Cosmetics, 86, pp. 112–115 (1971).
"Siloxane SWS-03314," SWS Silicones Corporation, Feb., 1975.
"Volatile Silicone 7158," Cosmetic Formulary, 1976.
"Volatile Silicone Fluids for Cosmetic Formulations," Todd, C. and Byers T., Cosmetics and Toiletries, 96(1), pp. 29–32(1976).
"Volatile Silicone 7207," Cosmetic Formulary, 1976.
Lutanol ®, IC and I Brochures BASF Feb. 1976 and Aug. 1977.
"Balsam Cream Rinse HF948A01," Exxon Chemical Technical Service Formula Sheet.
234297 2/17/81 Bolich et al. (patent applica.).

*Primary Examiner*—Delbert R. Phillips
*Assistant Examiner*—F. T. Moezie
*Attorney, Agent, or Firm*—Richard C. Witte; John V. Gorman; Douglas C. Mohl

[57] ABSTRACT

Hair conditioning compositions containing a volatile, liquid hair conditioning agent, which agent is thickened with a hydrophobic thickener.

15 Claims, No Drawings

HAIR CONDITIONING COMPOSITIONS

CROSS REFERENCE TO RELATED APPLICATION

This is a continuation-in-part of my copending application, Ser. No. 218,372, filed Dec. 22, 1980 which is a continuation-in-part of my copending application, Ser. No. 128,437, filed Mar. 10, 1980, both now abandoned.

TECHNICAL FIELD

The present invention is related to hair conditioning compositions which contain a volatile, liquid hair conditioning agent which is either a hydrocarbon or silicone and a hydrophobic thickener.

Volatile agents useful in hair conditioning compositions, while attractive for many reasons, present problems if it is desired to thicken them. Thickening is oftentimes attractive for cosmetic reasons.

BACKGROUND ART

The use of volatile agents in hair conditioning products is known. U.S. Pat. No. 3,577,528, May 4, 1971 to McDonough discloses two phase hair conditioners comprising an aqueous phase which contains a quaternary compound and a hydrocarbon or fluorinated hydrocarbon water immiscible phase. Rudy et al in U.S. Pat. No. 3,932,610, Jan. 13, 1976 discloses a shampoo composition which may contain a volatile hydrocarbon solvent. U.S. Pat. No. 3,818,105, June 18, 1974 to Coopersmith et al discloses hair conditioners containing a $C_{12}$ to $C_{14}$ isoparaffinic hydrocarbon fraction. South African Patent Application 666421, Apr. 12, 1967, Dasher and Fainer, discloses hair conditioners containing volatile silicones.

While these references disclose compositions which contain components of the type present in the compositions of the present invention, they are not entirely satisfactory, most often lacking in performance.

It is therefore an object of the present invention to provide hair conditioners which overcome problems associated with prior compositions.

It is a further object of the present invention to provide an improved method of conditioning hair.

These and other objectives will become more apparent from the disclosure which follows.

DISCLOSURE OF THE INVENTION

The present invention relates to hair conditioning compositions comprising from about 1% to about 99% of a volatile hydrocarbon or silicone agent and up to about 1% of a hydrophobic polymeric thickening agent.

DETAILED DESCRIPTION OF THE INVENTION

The compositions of the present invention comprise the above described essential components and may additionally contain several optical components. Each of the components is discussed in detail below.

Volatile Agent

The hydrocarbon and silicone agents useful in the present compositions have a boiling point in the range of about 99° C. to about 260° C. and have a solubility in water of less than about 0.1%. The hydrocarbons may be either straight or branched chain and may contain from about 10 to about 16, preferably from about 12 to about 16 carbon atoms. Examples of suitable hydrocarbons are decane, dodecane, tetradecane, tridecane and mixtures thereof.

The volatile silicones useful in the compositions of the present invention may be either a cyclic or a linear polydimethylsiloxane. The number of silicon atoms in the cyclic silicones is preferably from about 3 to about 7, more preferably 4 or 5.

The general formula for such silicones is

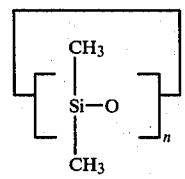

wherein n = 3–7

The linear polydimethylsiloxanes have from about 3 to 9 silicon atoms and have the general formula

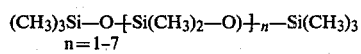

Silicones of the above type, both cyclic and linear, are offered by Dow Corning Corporation, Dow Corning 344, 345 and 200 fluids, Union Carbide, Silicone 7202 and Silicone 7158, and Stauffer Chemical, SWS-03314.

The linear volatile silicones generally have viscosities of less than about 5 centistokes at 25° C. while the cyclic materials have viscosities less than about 10 centistokes. "Volatile" means that the material has a measurable vapor pressure. A description of volatile silicones is found in Todd and Byers, "Volatile Silicone Fluids for Cosmetics", *Cosmetics and Toiletries*, Vol. 91, January, 1976, pp. 27–32, incorporated herein by reference.

The volatile agent is present in the compositions of this invention at a level of from about 1% to about 99%, preferably from about 2% to about 60%, more preferably from about 2% to about 10%. The volatile silicones are the preferred agents.

Hydrophobic Thickening Agent

The volatile hair conditioning agents of the present invention are thickened with a hydrophobic thickening agent having a mass average molecular weight of up to about 5,000,000, preferably from about 50,000 to about 5,000,000. The hydrophobic agents cause the volatile agent to feel less only on the hair.

Hydrocarbons are generally easier to thicken than volatile silicones although certain thickeners work equally well with either material. Examples of materials which work particularly well with hydrocarbons are poly(1-butene), polyisoprene, polybutadiene, ethylene/propylene copolymers, polyisobutylene, polyvinyl isobutyl ether and poly (ethylene-ethyl acrylate).

Thickeners which work particulrly well with volatile silicones include the above mentioned polyvinyl isobutyl ether as well as polyvinyl ethyl ether and the non-volatile polydimethylsiloxanes having a mass average molecular weight of up to about 5,000,000. The preferred thickeners are the polyvinylethers, most preferably polyvinyl isobutyl ether.

The hydrophobic thickening agent is present in the compositions of the present invention at a level of up to about 1%, preferably from about 0.005% to about 1.0%, most preferably from about 0.005% to about 0.5%.

Optional Components

In addition to the above described essential components the compositions of the present invention may contain a wide variety of optional components. Some of the most preferred optional components are described in detail below.

Water is a preferred optional component in the present compositions. Water is particularly useful when certain of the other water soluble optional components described below are included. The amount of water is not critical but is generally at a level of up to about 95%, preferably from about 75% to about 90%.

A water soluble thickening agent useful in the present compositions is a nonionic water soluble polymer. Included among such polymers are guar gum, locust bean gum, starches and starch derivatives such as hydroxyethyl amylose and starch amylose. Preferred polymers are guar gum and hydroxypropyl guar gum.

A cationic hair conditioning agent useful in the present compositions may be either a quaternary ammonium salt or the salt of a fatty amine.

Quaternary ammonium salts have the formula:

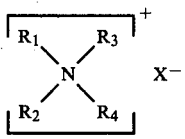

wherein $R_1$ is hydrogen, an aliphatic group of from 1 to 22 carbon atoms, or aromatic, aryl or alkaryl groups having from 12 to 22 carbon atoms, $R_2$ is an aliphatic group having 1-22 carbon atoms; $R_3$ and $R_4$ are each alkyl groups of from 1 to 3 carbon atoms, and X is a anion selected from halogen, acetate, phosphate, nitrate and methyl sulfate radicals. The aliphatic groups may contain, in addition to carbon and hydrogen atoms, ether linkages as well as amido groups among other groups.

Preferred quaternary ammonium salts are the dialkyl dimethyl ammonium chlorides, wherein the alkyl groups have from 12 to 22 carbon atoms and are derived from long-chain fatty acids, such as hydrogenated tallow. The term "tallow" refers to fatty alkyl groups derived from tallow fatty acids. Such fatty acids give rise to quaternary compounds wherein $R_1$ and $R_2$ have predominately from 16 to 18 carbon atoms. The term "coconut" refers to fatty acid groups from coconut oil fatty acids. The coconutalkyl $R_1$ and $R_2$ groups have from about 8 to about 18 carbon atoms and predominate in $C_{12}$ to $C_{14}$ alkyl groups.

Representative examples of quaternary ammonium salts of the invention include ditallow dimethyl ammonium chloride; ditallow dimethyl ammonium methyl sulfate; dihexadecyl dimethyl ammonium chloride; di(-hydrogenated tallow) dimethyl ammonium chloride; dioctadecyl dimethyl ammonium chloride; dieicosyl dimethyl ammonium chloride; didocosyl dimethyl ammonium chloride; di(hydrogenated tallow) dimethyl ammonium acetate; dihexadecyl diethyl ammonium chloride; dihexadecyl dimethyl ammonium acetate; ditallow dipropyl ammonium phosphate; ditallow dimethyl ammonium nitrate; di(coconutalkyl)dimethyl ammonium chloride; and stearyl dimethyl benzyl ammonium chloride.

Other quaternary ammonium salts useful herein are the compounds of the formula

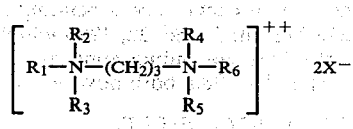

wherein $R_1$ is an aliphatic group having 16 to 22 carbon atoms, $R_2$, $R_3$, $R_4$, $R_5$ and $R_6$ are the same or different and are selected from H and alkyls having 1-4 carbon atoms and X is an anion as above defined. Tallow propanediammonium dichloride is an example of this quaternary ammonium salt.

Quaternary imidazolinium salts have the formula

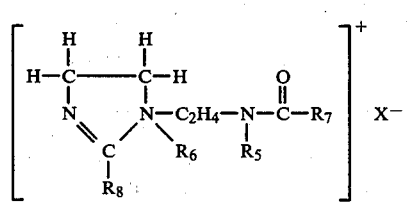

wherein $R_6$ is an alkyl group containing from 1 to 4, preferably from 1 to 2 carbon atoms, $R_5$ is an alkyl group containing from 1 to 4 carbon atoms or a hydrogen radical, $R_8$ is an alkyl group containing from 1 to 22, preferably at least 15 carbon atoms or a hydrogen radical, $R_7$ is an alkyl group containing from 8 to 22, preferably at least 15 carbon atoms, and X is an anion, preferably chloride. Other suitable anions include those disclosed with reference to the quaternary ammonium salts described hereinbefore.

Particularly preferred are those imidazolinium salts in which both $R_7$ and $R_8$ are alkyl of from 12 to 22 carbon atoms, e.g., 1-methyl-1-[(stearoylamide)ethyl]-2-heptadecyl-4, 5-dihydroimidazolinium chloride; 1-methyl-1-[(palmitoylamide)ethyl]-2-octadecyl-4,5-dihydroimidazolinium chloride and 1-methyl-1-[(tallowamide)-ethyl]-2-tallow-imidazolinium methyl sulfate.

Included as a suitable hair conditioner herein are salts of fatty amines. As used herein the amines may be primary, secondary or tertiary but the alkyl, substituted and unsubstituted groups preferably have from 12-22 carbon atoms. Preferred are the primary and secondary amines with the primary being the most preferred. Diamines having a long chain alkyl group may also be used. Examples of amines suitable for use include dimethyl stearamine, dimethyl soyamine, stearylamine, soyamine, myristylamine, tridecylamine, ethyl stearylamine, N-tallow propanediamine ethoxylated (5 moles E.O.) stearylamine dihydroxyethyl stearylamine and arachidylbehenylamine. The anions of the salts include those mentioned previously for the quaternary ammonium salts. Specific amine salts include stearylamine hydrochloride, soyamine chloride, stearylamine formate and N-tallow propanediamine dichloride.

The cationic hair conditioning agent, if present, is used at a level of from about 0.05% to about 4%, preferably from about 0.1% to about 2%.

Other optional components can be materials which are soluble in the volatile agent phase, in the aqueous phase or not soluble in either phase.

Included among materials soluble in the volatile agent phase are waxes such as cetyl alcohol and paraffin, and oils such as mineral oil and isopropyl myristate. Agents which are soluble in the aqueous phase include acrylamide and polyoxyethylene resins.

Among other optional components are dyes, perfumes, opacifiers, pearlescent aids, buffers, preservatives, antioxidants, and antidandruff aids such as zinc pyrithione and sulfur.

Method of Manufacture

There are many approaches suitable for making the present compositions. If it is desired to form an emulsion, the compositions should be processed in such a manner that the volatile agent is dispersed in the aqueous phase in particles of from about 1 to about 10 microns.

The preferred manner in which the hydrophobic thickener is incorporated into the present compositions is by preblending with the volatile liquid hair conditioning agent. This is accomplished by mixing the two together with agitation and heat until the thickener has completely dissolved. In the case of emulsions this preblend can be added to the aqueous phase or vice versa. Suitable processes are shown in the Examples.

Industrial Applicability

The hair conditioning compositions of the present invention are preferably used as a rinse on freshly shampooed hair. The composition is used in an amount of from about 1 g. to about 60 g., preferably from about 2 g. to about 30 g. and is then rinsed from the hair.

The following examples further describe and demonstrate embodiments within the scope of the present invention. The examples are given solely for the purpose of illustration and are not to be construed as limitations of the present invention as many variations thereof are possible without departing from its spirit and scope.

Unless otherwise indicated, all percentages herein are by weight.

EXAMPLE I

The following composition is prepared:

| | |
|---|---|
| Dow Corning Fluid 345[1] (cyclic silicone having 5 dimethyl siloxane groups) | 7.00% |
| Lutonal 1C 115[2] (polyvinyl isobutyl ether) | 0.02 |
| Corn Starch Powder[3] | 3.50 |
| Stearyl benzyl dimethyl ammonium chloride[4] | 0.30 |
| Ethanol | 7.00 |
| Distilled water     q.s. | 100.00% |

[1]Supplied by Dow Corning Corporation.
[2]Supplied by BASF.
[3]Supplied by CPC International, Inc.
[4]Supplied by Hexel-Fine Organics.

The above composition is prepared by dispersing 35 grams of starch powder in 822 grams of distilled water using a Lightnin ® Mixer. The mixture is heated to about 65° C. to fully dissolve and hydrate the starch. Three grams of the quaternary compound are then added, followed by the silicone/ether preblend. This preblend is prepared earlier by adding 0.2 g of Lutonal 1 C 115 to 70 grams of Dow Corning Fluid 345 and heating this to 60° C. with agitation for twelve hours by which time the ether is all dissolved. A high shear mixer, an Ultra Turrax ® Model 45S4 dispersator supplied by Tekmer Company, was finally used to further reduce the silicone/ether particle size to about 1 to about 10 microns. The ethanol is added as the batch cools to room temperature.

EXAMPLE II

The following composition was prepared:

| | |
|---|---|
| Union Carbide 7158 Silicone Fluid[1] (cyclic silicone having 5 dimethyl siloxane groups) | 8.000% |
| Lutonal 1C 115[1] (polyvinyl isobutyl ether) | 0.008 |
| Jaguar HP-60[2] (hydroxypropyl guar gum) | 1.100 |
| Ethanol | 8.000 |
| Adogen 442[3] (90% active) | 0.240 |
| Perfume | 0.500 |
| Distilled Water     q.s. | 100.000% |

[1]Supplied by Union Carbide Corporation
[2]Supplied by Stein-Hall.
[3]Di hydrogenated tallow dimethyl ammonium chloride supplied by Sherex Chemical Company.

The above composition was prepared by placing 76.08 grams of the volatile silicone, 400 grams of distilled water and 4 grams of a stock solution consisting of 2% Lutonal 1 C 115 in volatile silicone into a mix tank. The stock solution had been prepared earlier by dissolving 2 grams of the ether in 98 grams of the volatile silicone and mixing with a magnetic stirrer for 24 hours. A pre-mix was prepared by dispersing 2.4 grams of the quaternary and 11 grams of Juguar HP-60 in 80 grams of ethanol. This was mixed with a magnetic stirrer for 10 minutes at ambient temperature. This pre-mix was then added to the main mix tank and sheared with a Ultra Turrax Model 45S4 for five minutes. To the batch were then added 421 grams of distilled water and 5 grams of perfume. A Lightnin ® mixer was used to complete mixing the batch for 15 minutes.

What is claimed is:

1. A hair conditioning composition comprising:
   (A) from about 1% to about 99% of a volatile liquid hair conditioning agent selected from the group consisting of hydrocarbons, silicones and mixtures thereof; and
   (B) from about 0.005% to about 1% of a hydrophobic thickening agent having a mass average molecular weight of from about 50,000 to 5,000,000.

2. A hair conditioning composition according to claim 1 wherein the volatile liquid hydrocarbon hair conditioning agent is selected from the group consisting of decane, dodecane, tridecane, tetradecane and mixtures thereof.

3. A hair conditioning composition according to claim 2 wherein the volatile liquid hair conditioning agent is a silicone and is present at a level of from about 2% to about 60%.

4. A hair conditioning composition according to claim 3 wherein the amount of volatile liquid hair conditioning agent is from about 2% to about 10% and the amount of hydrophobic thickening agent is from 0.005% to about 0.5%.

5. A hair conditioning composition according to claim 4 wherein the hydrophobic thickening agent is selected from the group consisting of polyvinylisobutyl ether, polyvinyl ethyl ether, nonvolatile polydimethylsiloxanes and mixtures thereof.

6. A hair conditioning composition according to claim 5 wherein the volatile liquid hair conditioning agent is a cyclic silicone having either 4 or 5 dimethyl siloxane groups.

7. A hair conditioning composition according to claim 6 wherein the hydrophobic thickening agent is polyvinyl isobutyl ether.

8. A hair conditioning composition according to claim 7 wherein the volatile liquid silicone hair conditioning agent has 5 dimethyl siloxane groups.

9. A hair conditioning composition according to claim 8 which in addition contains from about 75% to about 95% water and from about 0.05% to about 4% of a cationic hair conditioning agent selected from the group consisting of quaternary ammonium salts and salts of fatty amines.

10. A method of conditioning hair comprising:
I. applying from about 1 g. to about 60 g. of a composition comprising
   (A) from about 1% to about 99% of a volatile liquid hair conditioning agent selected from the group consisting of hydrocarbons, silicones and mixtures thereof; and
   (B) from about 0.005% to about 1% of a hydrophobic thickening agent having a mass average molecular weight of up to 5,000,000.

11. A method according to claim 10 wherein the amount of volatile liquid hair conditioning agent is from about 2% to about 10% and the amount of hydrophobic thickening agent is from about 0.005% to about 0.5%.

12. A method according to claim 11 wherein the volatile liquid hair conditioning agent is a silicone and the hydrophobic thickening agent selected from the group consisting of polyvinylethylether, polyvinyl isobutyl ether, nonvolatile polydimethylsiloxanes and mixtures thereof.

13. A method according to claim 12 wherein the volatile liquid hair conditioning agent is a cyclic silicone having either 4 or 5 dimethylsiloxane groups.

14. A method according to claim 13 wherein the volatile liquid hair conditioning agent is a cyclic silicone having 5 dimethyl siloxane groups and the hydrophobic thickening agent is polyvinyl isobutyl ether.

15. A method according to claim 14 wherein the composition contains in addition from about 75% to about 95% water and from about 0.05% to about 4.0% of a cationic hair conditioning agent selected from the group consisting of quaternary ammonium salts and salts of fatty amines.

* * * * *

UNITED STATES PATENT OFFICE
CERTIFICATE OF CORRECTION

PATENT NO. : 4,387,090

DATED : June 7, 1983

INVENTOR(S) : Raymond E. Bolich, Jr.

It is certified that error appears in the above-identified patent and that said Letters Patent are hereby corrected as shown below:

Column 7, line 24, delete "."

Column 7, line 25, insert "to freshly shampooed hair; and
   II. rinsing the composition from the hair."

Signed and Sealed this

Nineteenth Day of March 1985

[SEAL]

Attest:

DONALD J. QUIGG

Attesting Officer    Acting Commissioner of Patents and Trademarks